(12) United States Patent
Hegg

(10) Patent No.: US 11,529,504 B2
(45) Date of Patent: Dec. 20, 2022

(54) DYNAMIC GAS-FLOW WOUND DRESSING ASSEMBLY AND METHOD FOR ENHANCING THE EFFECT OF GENERATED GAS FLOW ACROSS A WOUND

(71) Applicant: Jeffrey Wayne Hegg, Saint Petersburg, FL (US)

(72) Inventor: Jeffrey Wayne Hegg, Saint Petersburg, FL (US)

( * ) Notice: Subject to any disclaimer, the term of this patent is extended or adjusted under 35 U.S.C. 154(b) by 443 days.

(21) Appl. No.: 16/794,189

(22) Filed: Feb. 18, 2020

(65) Prior Publication Data

US 2020/0269028 A1 Aug. 27, 2020

Related U.S. Application Data

(60) Provisional application No. 62/811,242, filed on Feb. 27, 2019.

(51) Int. Cl.
*A61M 35/00* (2006.01)
*A61F 13/00* (2006.01)

(52) U.S. Cl.
CPC ....... *A61M 35/30* (2019.05); *A61F 13/00029* (2013.01); *A61F 13/00042* (2013.01); *A61F 13/00068* (2013.01); *A61M 2202/0208* (2013.01)

(58) Field of Classification Search
CPC ........... A61M 35/30; A61M 2202/0208; A61F 13/00029; A61F 13/00042; A61F 13/00068
See application file for complete search history.

(56) References Cited

U.S. PATENT DOCUMENTS

| | | | | |
|---|---|---|---|---|
| 3,881,477 A | * | 5/1975 | Von Otto | ............... A61B 90/40 128/200.24 |
| 5,154,697 A | | 10/1992 | Loor | |
| 5,693,068 A | * | 12/1997 | Kuhlman | .............. A61F 15/008 604/304 |

(Continued)

FOREIGN PATENT DOCUMENTS

EP 3287106 A1 2/2018

*Primary Examiner* — Susan S Su
*Assistant Examiner* — Eric Rassavong
(74) *Attorney, Agent, or Firm* — Mark C. Johnson; Johnson Dalal

(57) ABSTRACT

A dynamic gas-flow wound dressing assembly and method for enhancing the effect of generated gas flow across a wound creates spacing between a medical dressing cover and the wound to enhance ventilation. The assembly provides a medical dressing cover that covers a wound. The medical dressing couples to a gas flow framing structure having a gas inlet and enclosed gas outlets. A high rate gas flow is introduced through gas flow framing structure. The gas discharges to cross the wound. A scaffolding partition member serves as a resilient spacer between the gas flow framing structure and wound, enhancing ventilation by forces on the skin and directing gas flow. The scaffolding includes intake ports and outlet ports in fluid communication with inlets and outlets of gas flow framing structure. The scaffolding carries generated gas flow from the gas flow framing structure to wound, covering a larger gas flow volume across wound.

17 Claims, 10 Drawing Sheets

(56) References Cited

U.S. PATENT DOCUMENTS

| | | | | |
|---|---|---|---|---|
| 5,702,356 A | * | 12/1997 | Hathman | A61F 13/0206 |
| | | | | 602/41 |
| 6,465,708 B1 | * | 10/2002 | Augustine | A61M 35/00 |
| | | | | 602/41 |
| 7,263,814 B2 | | 9/2007 | Rosati | |
| 8,708,982 B2 | | 4/2014 | Lin | |
| 8,945,030 B2 | * | 2/2015 | Weston | A61M 1/90 |
| | | | | 604/289 |
| 8,978,265 B2 | * | 3/2015 | Parker | A61F 13/00051 |
| | | | | 604/320 |
| D744,639 S | | 12/2015 | Aklog | |
| 9,554,946 B2 | | 1/2017 | Tang et al. | |
| 2011/0015565 A1 | * | 1/2011 | Hursey | A61M 35/30 |
| | | | | 604/24 |
| 2011/0276016 A1 | * | 11/2011 | Tsai | A61M 1/966 |
| | | | | 604/319 |
| 2012/0022436 A1 | * | 1/2012 | Bradley | A61M 35/30 |
| | | | | 604/23 |
| 2012/0197220 A1 | * | 8/2012 | Huang | A61M 35/30 |
| | | | | 604/305 |
| 2016/0361478 A1 | | 12/2016 | Eddy | |
| 2019/0030224 A1 | * | 1/2019 | Lin | A61L 15/26 |

* cited by examiner

DYNAMIC GAS-FLOW WOUND DRESSING ASSEMBLY AND METHOD FOR ENHANCING THE EFFECT OF GENERATED GAS FLOW ACROSS A WOUND

CROSS-REFERENCE TO RELATED APPLICATION

This application claims priority to U.S. Provisional Patent Application No. 62/811,242, filed Feb. 27, 2019, the entirety of which is incorporated by reference.

FIELD OF THE INVENTION

The present invention relates generally to medical wound dressings, and, more particularly, relates to adaptors for medical wound dressings having dynamic gas flow capability.

BACKGROUND OF THE INVENTION

Typically, treating a wound on the skin requires the application of a homogenous wound dressing, often made of woven cotton threads. The wound dressing is laid over the entire wound area to keep the wound clean, and to protect the wound from external contaminants and direct physical trauma. The dressing is also useful for absorbing bodily fluids from the wound, while maintaining a level of ventilation.

Wound treatment also utilizes Topical Oxygen Therapy (TOT) through the application of oxygen gas to the wound surface. Hyperbolic Oxygen Therapy (HBOT) is primarily prescribed treatment technic. An Apr. 3, 2017 Centers for Medicare & Medical Services (CMS) decision memo addresses TOT reimbursement policies because of the wound recovery improvements seen in published data. The dynamic distribution of gas over a wound at high flow rates (greater than 1 litter/min) is enabled by Bandage/Diaper Aeration Device as described in U.S. Pat. No. 8,978,265. As described this liner device is attached to the wound cover and the gas flow distribution follows the contour of the wound cover rather than the wound contour thereby not achieving optimum healing effect of the gas flow.

The use of foam material that act as a barrier between the wound and the wound dressing is well known. The barrier achieves an interface to the treatment area that increases the volume of the treated area by moving the wound dressing further from the wound by the thickness of the barrier. These barrier configurations can be manufactured using foam-based products used for multiple medical device applications. The manufacturing and material process of the barrier is common to such medical device applications.

When a medical grade foam barrier is used between the wound dressing and the wound in TOT therapy, a larger gas flow treatment volume, more space between the liner and the skin and additional padding between the wound dressing and the skin is provided. As such, the flow from the liner device flows into the larger treatment volume created by the barrier. Therapeutic value of the gas flow is improved through control of the gas flow to targeted areas of treatment.

Therefore, a need exists to overcome the problems with the prior art as discussed above.

SUMMARY OF THE INVENTION

The invention provides a dynamic gas flow wound dressing assembly and method for enhancing the effect of generated gas flow across a wound that overcomes the hereinafore-mentioned disadvantages of the heretofore-known devices and methods of this general type and that creates spacing between a medical dressing cover and the wound, so as to enhance ventilation; and also discharges a generated gas flow from the increased spacing, so as to increase the gas flow volume across the wound.

In some embodiments, the wound dressing assembly provides a medical dressing cover that is adapted to cover a wound on the skin, create ventilation, and absorbing bodily fluids therefrom. The medical dressing cover couples to a gas flow framing structure having a gas inlet and enclosed gas outlets. A high rate gas flow is introduced through the gas flow framing structure to cross the wound for enhanced wound treatment.

The dynamic gas flow wound dressing assembly also provides a unique scaffolding partition member that serves as a secondary attachment to the gas flow framing structure. The scaffolding partition member serves as a resilient spacer between the gas flow framing structure and the wound, which enhances ventilation across the wound.

The scaffolding partition member also serves to carry the generated gas flow from the gas flow framing structure. The scaffolding partition member includes intake ports and outlet ports that are in fluid communication with the inlets and outlets of the gas flow framing structure. The gas flow discharges from the outlet ports of the scaffolding partition member, covering a larger gas flow area and volume across the wound. Further, the scaffolding partition member may be fabricated from a resilient foam, medical-grade material that enables facilitated deformation to match the contours of the skin near the wound.

The present invention is an augmentation of the therapy system by using the scaffolding partition member that enhances the effect of the gas flow in the treatment areas. The scaffolding partition member can be a structural element or alternatively provide gas flow ducting features to follow a patient skin contour.

With the foregoing and other objects in view, there is provided, in accordance with the invention, a dynamic gas-flow wound dressing assembly comprising a medical dressing covering having an upper surface, a lower surface opposing the upper surface.

The dynamic gas-flow wound dressing assembly further comprises a gas flow framing structure coupled to the medical dressing covering. The gas flow framing structure has an outer surface and an inner surface opposing the outer surface of the gas-flow framing structure. The inner surface defines a gas inlet, a gas flow channel within the gas-flow framing structure, and a plurality of enclosed gas outlets disposed on the inner surface of the gas-flow framing structure and downstream of the gas inlet. The plurality of enclosed gas outlets are each operably configured and oriented to provide a generated gas flow therethrough and to a framing area defined by the inner surface of the gas-flow framing structure and disposed proximal to the lower surface of the medical dressing covering.

The dynamic gas-flow wound dressing assembly further comprises a scaffolding partition member of a flexible material. The scaffolding partition member has a lower surface without any adhesive disposed thereon, an outer surface, an inner surface opposing the outer surface of the scaffolding partition member, and an upper surface opposing the lower surface of the scaffolding partition member.

The upper surface of the scaffolding partition member is adhesively mated to the lower surface of the gas flow framing structure, and defines an enclosed scaffolding treatment area and scaffolding treatment volume with the inner surface of the scaffolding partition member. The upper surface of the scaffolding partition member is selectively removably directly coupled to the gas-flow framing structure in a contouring configuration therewith.

In accordance with another feature, the scaffolding partition member is configured to apply forces on the skin to achieve an enlargement of the volume being treated.

In accordance with another feature, the scaffolding partition member is configured to direct the gas flow to a targeted treatment area.

In accordance with another feature, the scaffolding partition member is defined by a plurality of intake ports aligned with the plurality of enclosed gas outlets, a plurality of outlet ports, and at least one gas transportation channel internally disposed within the scaffolding partition member and fluidly coupled to the plurality of intake ports and the plurality of outlet ports.

In accordance with a further feature of the present invention, the gas-flow framing structure is enclosed and the upper surface of the scaffolding partition member is directly coupled to the gas-flow framing structure in a contouring configuration surrounding a perimeter defined thereon.

In accordance with a further feature of the present invention, the scaffolding partition member is substantially of a polymeric foam material having a deformably resilient property.

In accordance with a further feature of the present invention, the plurality of outlet ports of the scaffolding partition member are defined along the lower surface of the scaffolding partition member.

In accordance with a further feature of the present invention, the plurality of intake ports of the scaffolding partition member are defined along the upper surface of the scaffolding partition member.

In accordance with a further feature of the present invention, the scaffolding partition member comprises an edge having a height, the edge creating separation between the gas flow framing structure and a wound area on the skin.

In accordance with a further feature of the present invention, the scaffolding partition member further defines a first adaptor and a second adaptor having substantially the same shape and dimension, the first and second adaptors adapted to sandwich the gas flow framing structure in a contouring configuration surrounding the perimeter defined thereon. The scaffolding partition members apply forces to the wound treatment area to achieve a larger treatment volume.

In accordance with a further feature of the present invention, the scaffolding partition member further defines a wedge having a wide end and a narrow end, the narrow end that inserts into the treatment area to expose a larger surface for exposure to the gas flow.

In accordance with a further feature of the present invention, the scaffolding partition member further defines a C-shaped scaffold partition member having an outer face and an inner face, the outer face having a plurality of intake ports aligned with the plurality of enclosed gas outlets, a plurality of outlet ports, and at least one gas transportation channel internally disposed within the C-shaped scaffolding partition member and fluidly coupled to the plurality of intake ports and the plurality of outlet ports.

In accordance with a further feature of the present invention, the scaffolding partition member further defines a U-shaped scaffold partition member having an outer face that aligns the gas flow framing structure to direct the gas flow to the treatment area.

In accordance with a further feature of the present invention, the upper surface of the scaffolding partition member or the lower surface of the gas flow framing structure comprises an adhesive.

In accordance with a further feature of the present invention, the generated gas flow is vented at atmospheric pressure at the wound.

In accordance with the present invention, a method for enhancing the effect of generated gas flow across a wound area on the skin. The method includes an initial Step of identifying a wound area on the skin.

Another Step may include coupling a gas flow framing structure to a medical dressing covering, the gas flow framing structure defining a gas inlet, a gas flow channel within the gas-flow framing structure, and a plurality of enclosed gas outlets operably configured and oriented to direct a generated gas flow therethrough.

Yet another Step of the method comprises deforming a resilient scaffolding partition member to fit the contours of the skin near the wound, the scaffolding partition member having an edge defined by a height, the edge creating separation between the gas flow framing structure and the wound area. The scaffolding partition member further having a configuration to open the wound treatment volume by applying forces to the skin, a configuration to direct the gas flow in a desired direction or a plurality of intake ports a plurality of outlet ports, and at least one gas transportation channel internally disposed within the scaffolding partition member and fluidly coupled to the plurality of intake ports and the plurality of outlet ports.

The method may also include a Step of applying the scaffolding partition member to the gas flow framing structure applied to the wound or aligning the plurality of enclosed gas outlets of the gas-flow framing structure with the plurality of intake ports of the scaffolding partition member.

A Step comprises engaging the gas flow framing structure with the scaffolding partition member, whereby the edge of the scaffolding partition member creates separation between the medical dressing and the wound, whereby the scaffolding partition member being directly coupled to the gas-flow framing structure in a contouring configuration therewith.

In one embodiment, a Step includes introducing the generated gas flow into the gas inlet of the gas-flow framing structure, the generated gas flow is vented at atmospheric pressure.

A final Step comprises discharging the gas through the at least one gas transportation channel and the plurality of outlet ports of the scaffolding partition member, whereby the scaffolding partition member increases the volume of air flowing over the wound.

Although the invention is illustrated and described herein as embodied in a dynamic gas-flow wound dressing scaffolding adaptor, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the gas-flow framing structure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
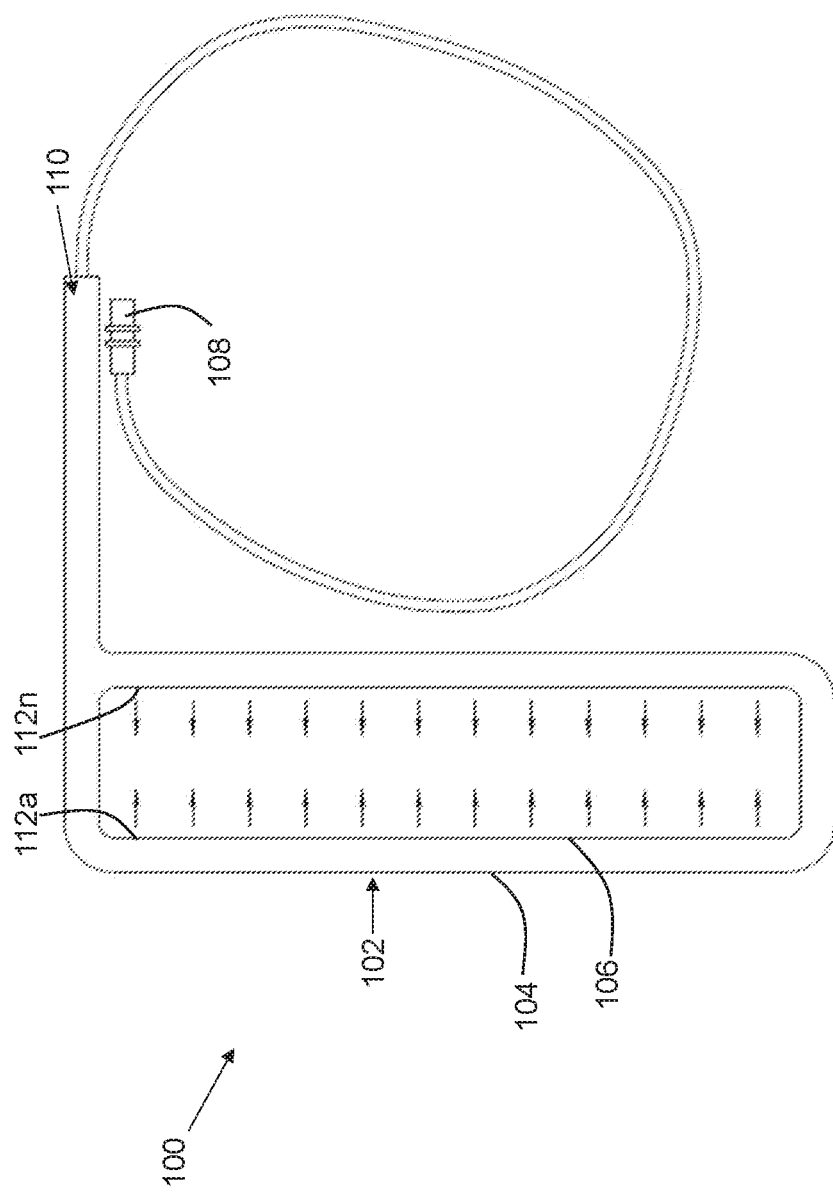
FIG. 1 is a top view of an exemplary gas flow framing structure, in accordance with an exemplary embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient dynamic gas flow wound dressing assembly 400 and method 1100 for enhancing the effect of generated gas flow across a wound that creates spacing between a medical dressing cover 200 and the wound 204, so as to enhance ventilation; and also discharges a generated gas flow from the increased spacing, so as to increase the gas flow volume across the wound. Embodiments of the invention provide a medical dressing cover 200 that dresses a wound 204 on the skin. In addition, embodiments of the invention provide a gas flow framing structure 102 coupled to the medical dressing cover 200 that discharges a generated gas flow 308 across the wound 204.

Additional embodiments include a scaffolding partition member 300 that serves as a secondary attachment to the gas flow framing structure 102. The scaffolding partition member 300 serves as a resilient spacer between the gas flow framing structure 102 and the wound 204, which enhances ventilation across the wound 204. The scaffolding partition member can apply forces to skin around the wound to expose more area and volume. The scaffolding partition member also can serve to direct the gas flow. The scaffolding partition member 300 can also serves to carry the generated gas flow 306 from the gas flow framing structure 102. The scaffolding partition member 300 includes intake ports 700a-n and outlet ports 702a-n that are in fluid communication with the gas inlet 108 and enclosed gas outlets 112a-n of the gas flow framing structure 102. The gas flow discharges from the outlet ports 702a-n of the scaffolding partition member 300, which covers a larger gas flow area and volume across the wound 204. Further, the scaffolding partition member 300 may be fabricated from a resilient foam, medical-grade material that enables facilitated deformation to match the contours of the skin near the wound. This allows for fitting to multiple parts of the body, including fitting inside folds of skin/fat.

Figure 2:
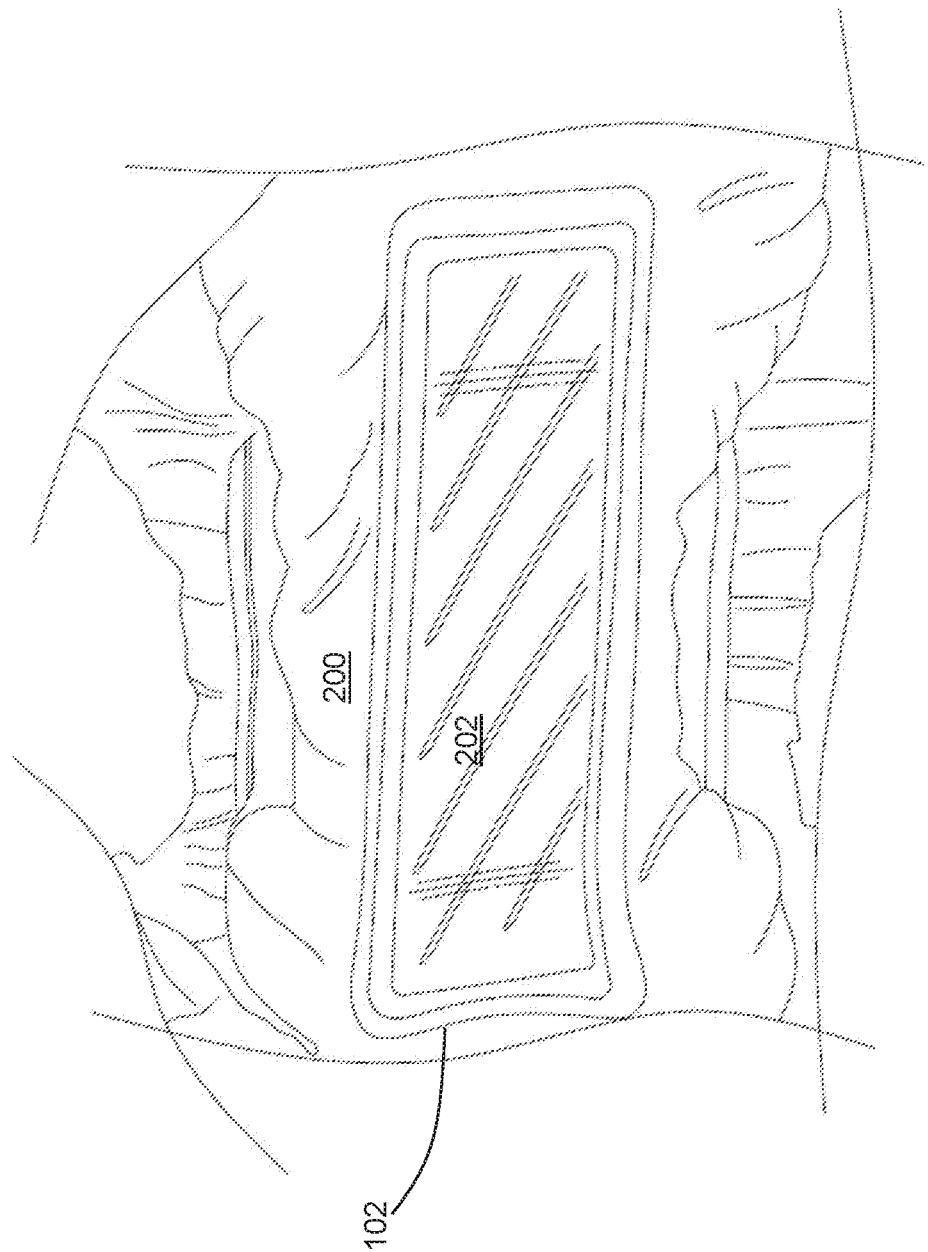
FIG. 2 is a perspective view of an exemplary medical dressing cover, in accordance with an exemplary embodiment of the present invention.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components. FIG. 1 and FIG. 2 illustrate a gas-flow framing structure 102 that is configured to couple with a medical dressing cover 200, while introducing a high rate gas flow across a wound 204, so as to enhance treatment of the wound 204 with the gas. Those skilled in the art will recognize that oxygen flow over the wound, at atmospheric pressure, may increase the efficacy of healing a wound 204.

The gas-flow framing structure 102, as shown in FIG. 1, includes an outer surface 104 and an opposing inner surface 106. In some embodiments, the outer surface 104 may be oriented away from the wound 204 on the skin, while the inner surface 106 orients towards the wound 204, in the same orientation as the lower surface 202 of the medical dressing cover 200 (See FIG. 2). In one embodiment, the gas-flow framing structure defines a gas inlet 108 through which a generated gas flow is introduced. The gas inlet 108 may include a nozzle or simply an opening. The generated gas flow may be air, oxygen, or other regenerative gas, set at inlet pressure to cause the gas flow to vent at atmospheric pressure over the wound area from the gas-flow framing structure, which is known in the art to optimize enhancement of a wound on the skin. The generated gas flow may be sourced from a nebulizer, an oxygen concentrator or pressurized oxygen tank, as used in the medical field.

The inner surface 106 and the outer surface 102 of the gas-flow framing structure 102 also defines a gas flow channel 110 within the gas-flow framing structure 102. The gas flow channel 110 is in fluid communication with the gas inlet 108. A plurality of enclosed gas outlets 112a-n are disposed on the inner surface 106 of the gas-flow framing structure 102, downstream, and in fluid communication with the gas inlet 108. In some embodiments, the gas flow channel 110 may include a polymer, medical-grade tube that passes through the gas flow channel 110 of the body of the gas-flow framing structure 102. The enclosed gas outlets 112a-n serve as the discharge point from the gas-flow framing structure, and may comprise multiple, equally spaced-apart openings disposed across the inner surface 106 of the gas-flow framing structure 102. The equal spacing between enclosed gas outlets 112a-n helps create uniform gas flow distribution across the wound 204.

In some embodiments, the enclosed gas outlets 112a-n are each operably configured and oriented to direct the generated gas flow 306 to a framing area 308. The framing area 308 may be a simple enclosure that is defined by the inner surface 106 of the gas-flow framing structure 102, and which is disposed proximal to the lower surface 202 of the medical dressing covering 200. The framing area 308 covers the wound, such that the wound is substantially enclosed within the framing area 308.

In some embodiments, the shape and dimensions of the framing area 308 may be adapted to accommodate different parts of the body. For example, FIG. 1 shows the framing area 308 defined by a generally rectangular shape. Despite any shape of the framing area 308, the gas discharges approximately within the enclosed area of the inner surface 106. This requires that the wound is substantially enclosed within the framing area 308 so that the gas flow substantially crosses the wound area.

In some embodiments, the assembly 400 provides a medical dressing cover 200 that is adapted to cover a wound on the skin, create ventilation, and absorbing bodily fluids therefrom. A standard medical dressing cover 200 is shown in FIG. 2. In one non-limiting embodiment, the medical dressing cover 200 is a diaper. In another embodiment, the medical dressing cover 200 has a square or rectangular shape with a lower surface 202 and an opposing upper surface 302 such as gauze or medical wrapping. The upper surface 302 orients outwardly, being visible and accessible for manipulation and inspection of the medical dressing cover 200.

The medical dressing cover 200 is configured to work in conjunction with the gas flow framing structure 102. As shown in the illustration, the medical dressing cover 200 integrates with the gas flow framing structure 102, with each component providing a different, but important function for treating the wound. In this manner, the medical dressing cover 200 helps orient the gas flow framing structure, such that the framing area 308 and enclosed gas outlets 112a-n thereof, orient towards the wound. In one embodiment, the gas flow framing structure 102 is sewn or adhered, coplanar to the medical dressing cover 200, with both lower surfaces 106, 202 oriented towards the wound.

In operation, gas enters through a gas inlet 108 and is distributed to the wound via discrete valves into the treatment area. The gas flows to the outside of the medical dressing cover 200 to atmospheric pressure without any pressurization of the treatment area. The illustrated gas flow framing structure 102 is adhered to a medical dressing cover 200 that is a diaper. Those skilled in the art will also recognize that normal use of the medical dressing cover 200 is without the scaffolding partition member 300, described below. While the standard medical dressing cover 200 is rectangular in shape additional configurations, such as square, round or oval are possible.

Figure 3:
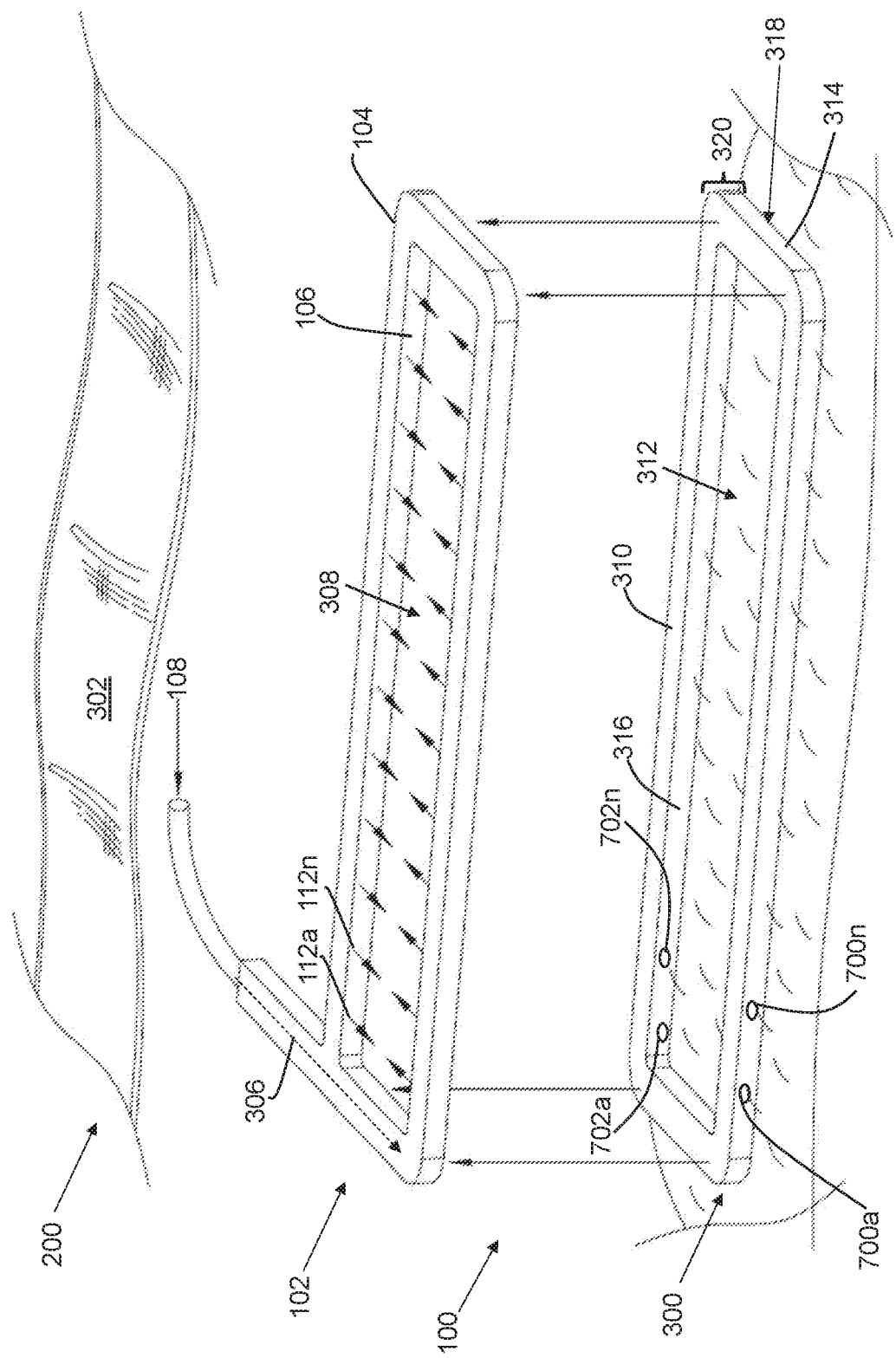
FIG. 3 is a perspective view of an exemplary dynamic gas flow wound dressing assembly, showing a scaffolding partition member with the gas flow framing structure and the medical dressing cover, in accordance with an exemplary embodiment of the present invention.

Turning now to FIG. 3, the assembly 400 also provides a unique scaffolding partition member 300 that serves as a secondary attachment to the gas flow framing structure 102. The scaffolding partition member 300 serves as a barrier between the wound and the medical dressing cover 200. Thus, the scaffolding partition member 300 is sufficiently resilient to form a snug, yet ventilated fit with eclectic contours, shapes, and deformations that form across the human body, while still receiving the body of the medical dressing cover 200 and the attached gas flow framing structure 102. In one embodiment the scaffolding partition member applies forces to the skin to allow gas flow from the gas flow framing structure into a larger scaffolding treatment area and increase access to difficult to treat skin areas. In another embodiment, the scaffolding partition member directs the gas flow from the gas flow framing structure into the scaffolding treatment area. In a third embodiment the scaffolding partition member provides ducting to guide the gas flow from the gas flow framing structure to the scaffolding treatment area. In some cases the scaffolding partition member and the gas flow framing structure are used without the medical dressing cover for cases without exudate and dry areas.

In one non-limiting embodiment, the scaffolding partition member 300 is fabricated substantially from a polymeric foam material that inherently has a deformably resilient property. Such resilience enables the scaffolding partition member 300 to be fitting into crevices, folds, and deformations of the body in and around the wound. This flexible fitting adaptation allows the scaffolding partition member 300 to snugly engage substantially any part of the body having a wound. However, in other embodiments, different types of resilient medical grade resilient material, known in the art, may be used to fabricate the scaffolding partition member 300. Thus, the scaffolding partition member 300 comprises a resilient, medical-grade material that enables facilitated deformation to match the contours of the skin and body near the wound.

Figure 4:
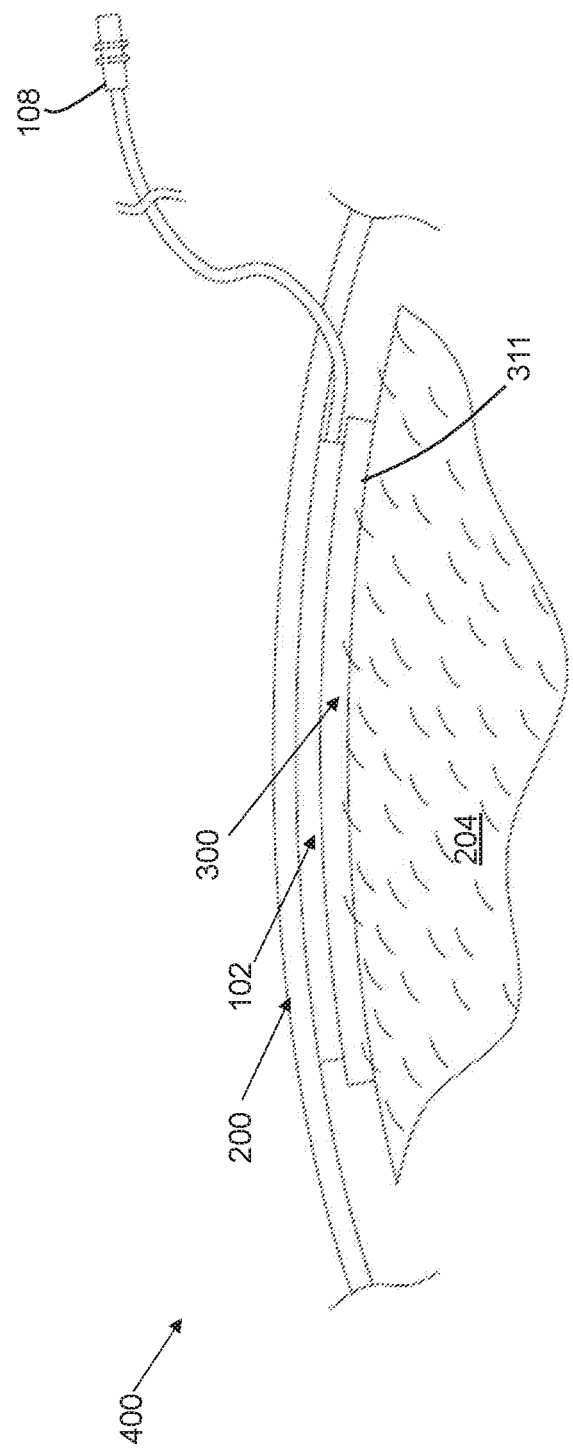
FIG. 4 is an elevated side view of the dynamic gas flow wound dressing assembly, showing the scaffolding partition member, gas flow framing structure, and medical dressing cover layered on the wound, in accordance with an exemplary embodiment of the present invention.

Looking now at FIG. 4, the scaffolding partition member 300 has a lower surface 311 that is adhesive-free, and oriented towards the wound. The scaffolding partition member 300 also has an upper surface 310 opposite the lower surface 311. And as shown back in FIG. 3, the edges of the scaffolding partition member 300 are defined by an inner surface 316 opposing an outer surface 314 of the scaffolding partition member 300. The upper surface 310 or the mating surface on the gas flow framing structure 102 has an adhesive material disposed thereon. The adhesive may be operable to securely fasten the scaffolding partition member 300 to the gas flow framing structure 102 and/or the medical dressing cover 200. Through adhesion, fasteners, or simply friction-fit coupling, the scaffolding partition member 300 and the gas flow framing structure 102 detachably couple to each other. Thus, the upper surface 310 of the scaffolding partition member 300 is selectively removably directly coupled to the gas-flow framing structure 102 in a contouring configuration therewith.

The upper surface 310 of the scaffolding partition member 300 is directly coupled to the gas-flow framing structure 102 in a contouring configuration surrounding a perimeter defined thereon. The upper surface 310 is also configured to define an enclosed scaffolding treatment area 312 and scaffolding treatment volume with the inner surface 316 of the scaffolding partition member 300.

In yet another embodiment, the enclosed scaffolding treatment area 312 of the scaffolding partition member 300 is sized and dimensioned approximate to the framing area 308 of the gas-flow framing structure 102. In this manner, the gas-flow framing structure 102 can be placed over the scaffolding partition member 300, such that the generated gas flow discharged from the enclosed gas outlets are substantially aligned with intake ports 700a-n that form along correlating surfaces of the scaffolding partition member 300 providing ducting from the gas flow framing structure to the scaffolding treatment area 312.

In another embodiment, the detachable coupling therebetween allows the scaffolding partition member 300 to serve as a resilient, size and shape-adjustable spacer between the gas flow framing structure 102 and the wound on the skin that produces force on the skin to provide a larger access to the scaffolding treatment area 312. Thus, as gas flows from the gas flow framing structure 102 towards the wound, the extra distance from the wound created by spacing from the scaffolding partition member 300 increases the gas flow across a larger volume of the wound, and creates a gap between the medical dressing cover and the wound that enhances ventilation.

In another embodiment the detachable coupling therebetween allows the scaffolding partition member to serve as a resilient, size and shape-adjustable spacer between the gas flow framing structure 102 and directs the gas flow in the direction of the wound surface within the scaffolding treatment area 312 rather that the direction the gas would flow if directed by the attachment to the medical dressing cover.

In one embodiment, the scaffolding partition member 300 comprises an edge 318 having a height 320. Since the scaffolding partition member 300 creates separation between the wound and the medical dressing cover 200, the height 320 of the edge 318 creates separation between the gas flowing from the gas flow framing structure 102 and the wound. In addition to serving as a spacer, the scaffolding partition member 300 also works to duct the generated gas flow 306 from the gas low framing structure 102 across the wound. The scaffolding partition member 300 is in fluid communication with regards to the generated gas flow entering the gas flow framing structure 102.

The use of foam material that act as a barrier between the wound and the medical dressing cover 200 such is shown in FIG. 4. The scaffolding partition member 300 achieves an interface to the treatment area that increases the volume of the treated area by moving the medical dressing cover 200 further from the wound by the height (thickness) of the scaffolding partition member 300. The configuration of the scaffolding partition member 300 can be manufactured using foam-based products used for multiple medical device applications. The manufacturing and material process of the scaffolding partition member 300 is common to such medical device applications as illustrated by the products produced by such companies as UFP Technologies.

Thus, when a medical grade foam scaffolding partition member 300 is used between the medical dressing cover 200 and the wound, a larger gas flow treatment volume, more space between the medical dressing cover 200 and the wound and additional padding between the medical dressing cover 200 and the wound is provided. As such, the flow from the gas valves flows into the larger treatment volume created by the scaffolding partition member 300.

In some embodiments, the scaffolding partition member 300 forms a plurality of intake ports 700a-n. The intake ports 700a-n align with the enclosed gas outlets 112a-n of the gas flow framing structure 102 when the gas flow framing structure 102 is engaged with the scaffolding partition member 300. In some embodiments, the plurality of intake ports are defined along the outer surface 314 of the scaffolding partition member 300. The scaffolding partition member 300 also forms a plurality of outlet ports 702a-n, and at least one gas transportation channel internally disposed within the scaffolding partition member 300 and fluidly coupled to the intake and outlet ports 700a-n, 702a-n. In some embodiments, the plurality of outlet ports are defined along the inner surface 316 of the scaffolding partition member 300. Thus, the intake and outlet ports 700a-n, 702a-n of the scaffolding partition member 300 may be in fluid communication with the gas inlet 108 and enclosed gas outlets 112a-n of the gas flow framing structure.

Consequently, gas discharges from the outlet ports 702a-n of the scaffolding partition member 300 onto the wound. This covers a larger gas flow area and volume across the wound than the enclosed gas outlets 112a-n of the gas flow framing structure 102 provide. This enhanced volume of gas coverage across the wound is a resultant of the additional spacing from the wound created by the scaffolding partition member 300; and also because of the orientation of the outlet ports 702a-n along the enclosed scaffolding treatment area 312. This guided discharge of gas over a larger area of the wound can result in significant reduction in healing time and the ability to improve the healing of wounds that previously were challenging to treat, for wounds such as diabetic ulcers, incontinent associated dermatitis, and rashes.

This gas ducting effect is achieved by aligning the enclosed gas outlets 112a-n from the gas flow framing structure 102 with the intake ports 700a-n of the scaffolding partition member 300. The outlet ports 702a-n of the scaffolding partition member 300 are ducted to the specific body location, patient size and wound configuration. There is no attachment to the skin nor pressure cavity formed by the scaffolding partition member 300. It is also significant to note that all of the gas pressure flows directly to atmospheric pressure with no gas pressure applied to the wound. In alternative embodiments, directional gas flow may be achieved by aligning the enclosed scaffolding treatment area 312, and the outlet ports 702a-n thereof, towards a volume that allows flow over the targeted treatment area.

Figure 5:
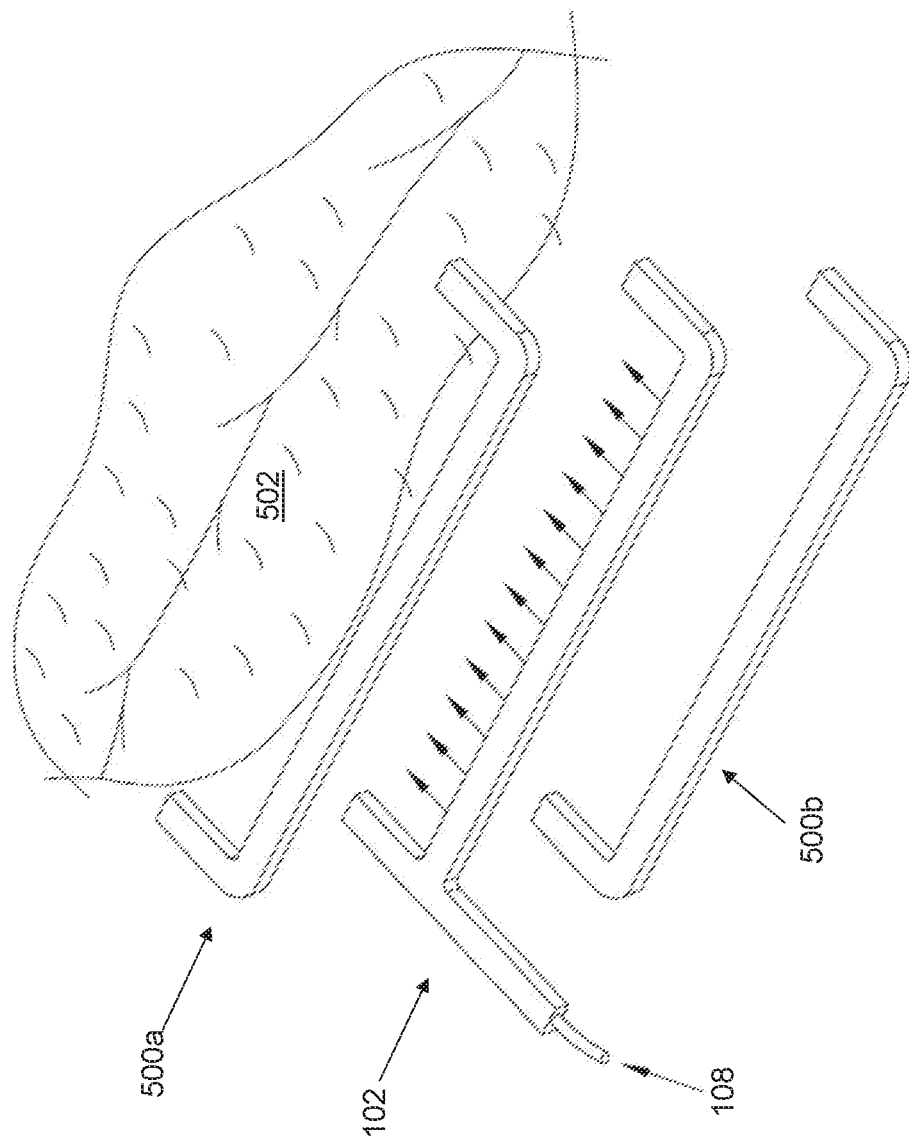
FIG. 5 is a perspective view of an alternative embodiment of the assembly, showing a first scaffolding partition member and a second scaffolding partition member sandwiching a folded gas flow framing structure inside a wound in a folded skin, in accordance with an exemplary embodiment of the present invention.
Figure 6:
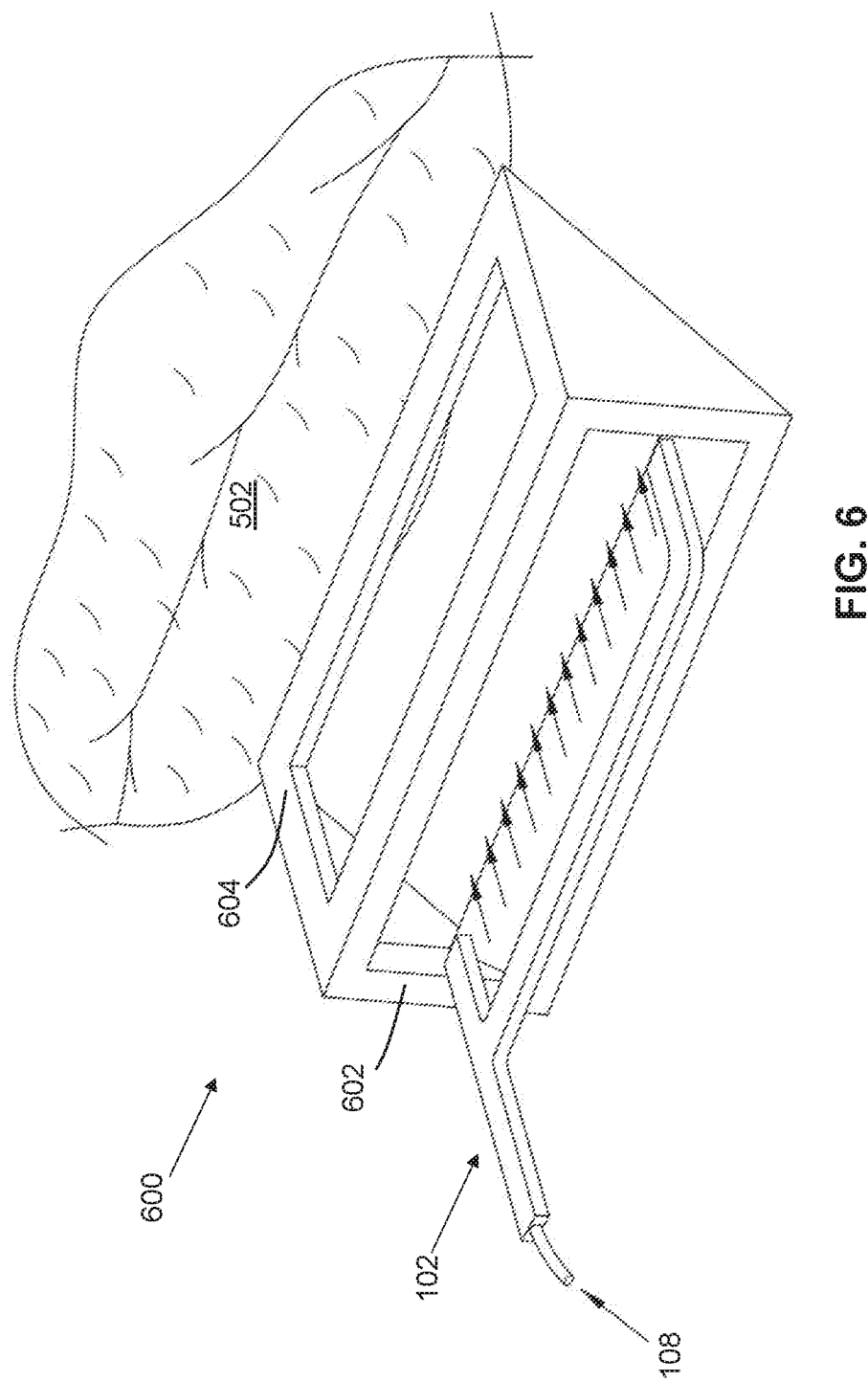
FIG. 6 is a perspective view of another alternative embodiment of the assembly, showing a wedge scaffolding partition member coupled to the gas flow framing structure, inside a wound in a folded skin, in accordance with an exemplary embodiment of the present invention.

FIGS. 5-6 illustrate alternative embodiments of the scaffolding partition member 300, for wounds that occur across folds in the skin. In this configuration, the gas flow framing structure 102 is folded back onto itself with its own adhesive along the long side, as shown for treatment of skin folds. In these embodiments, the scaffolding partition member 300 applies forces onto the skin achieving larger treatment areas by opening the skin fold for the gas to flow across a larger skin surface area. This embodiment may not need a medical dressing cover or may use a gauze wrapping or bandage as a medical dressing cover to hold the wound dressing assembly in place.

FIG. 5 shows the scaffolding partition member 300 bifurcated into a first adaptor 500a and a second adaptor 500b. The adaptors 500a-b are sized and dimensioned substantially the same, so as to match the dimensions of the gas flow framing structure when folded onto itself lengthwise. The resilient configuration of the adaptors 500a-b enables manipulation to fit into a folded skin 502 having a wound therein. In one embodiment, the identical first and second adaptors 500a-b are configured to sandwich the gas flow framing structure in a contouring configuration surrounding the perimeter defined thereon. As discussed above, this creates additional spacing for the generated gas flow to better access the wound by applying forces to the skin allowing improves gas flow within the scaffolding treatment area 312. Further, the spacing formed from the height of the adaptors 500a-b reduces heat and moisture buildup inside the folded skin 502. This embodiment may not need a medical dressing cover or may use a gauze wrapping or bandage as a medical dressing cover to hold the wound dressing assembly in place.

In yet another embodiment of the scaffolding partition member, shown in FIG. 6, the scaffolding partition member 300 defines a wedge 600 having a wide end 602 and a narrow end 604. A cavity forms in the wedge 600 to receive the inner surface 106 of the gas flow framing structure 102 for coupling thereto. The narrow end 604 is inserted into the skin fold to apply force to the skin that increases the volume of the scaffolding treatment area 312. Furthermore, wedge configuration allows the generated gas flow from the enclosed gas outlets to flow into the wedge shape to the wound area on the skin. It is evident from these examples that shape of the scaffolding partition member 300 can be customized for specific body areas. It is also significant to note that heat and moisture buildup inside the folded skin 502 is minimized. This embodiment may not need a medical dressing cover or may use a gauze wrapping or bandage as a medical dressing cover to hold the wound dressing assembly in place.

Figure 7:
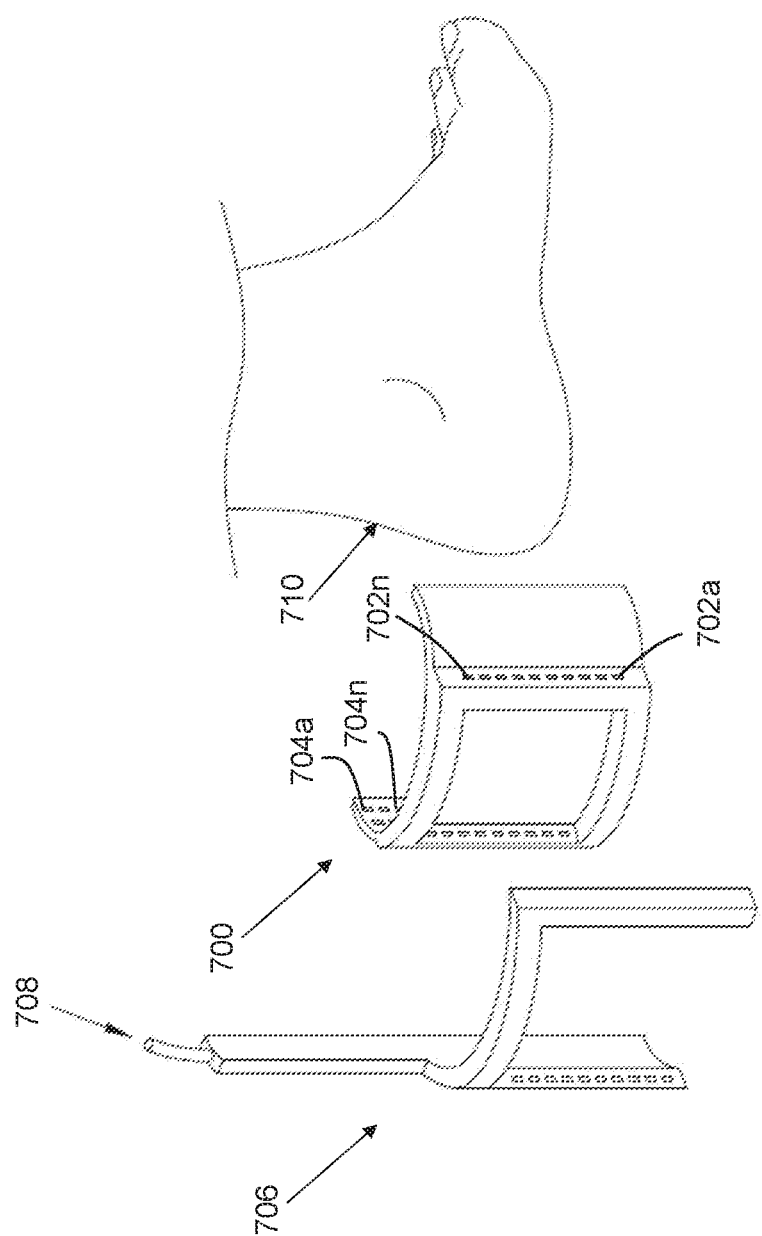
FIG. 7 is a perspective view of another alternative embodiment of the assembly, showing a C-shaped scaffold partition member that is adapted to fit around the heel, in accordance with an exemplary embodiment of the present invention.

Turning now to FIG. 7, the scaffolding partition member is configured into a C-shaped scaffold partition member 700 that is adapted to fit around the heel 710, where a wound requires treatment. The C-shaped scaffold partition member 700 has an outer face and an inner face. The outer face forms a plurality of intake ports 702a-n aligned with gas outlets from a correlating C-shaped gas flow framing structure 706. The outer face also forms a plurality of outlet ports 704a-n fluidly coupled to the plurality of intake ports and gas outlets. In one non-limiting embodiment, the C-shaped gas flow framing structure 706 is folded along the short side, and then adhered to the C-shaped scaffolding partition member 700. A gas inlet 708 introduces the generated gas flow 306 into the C-shaped gas flow framing structure 706 for discharge by the C-shaped scaffold partition member 700 onto the heel 710. This embodiment typically uses a medical dressing cover gauze that is wrapped around the entire wound dressing.

Figure 8:
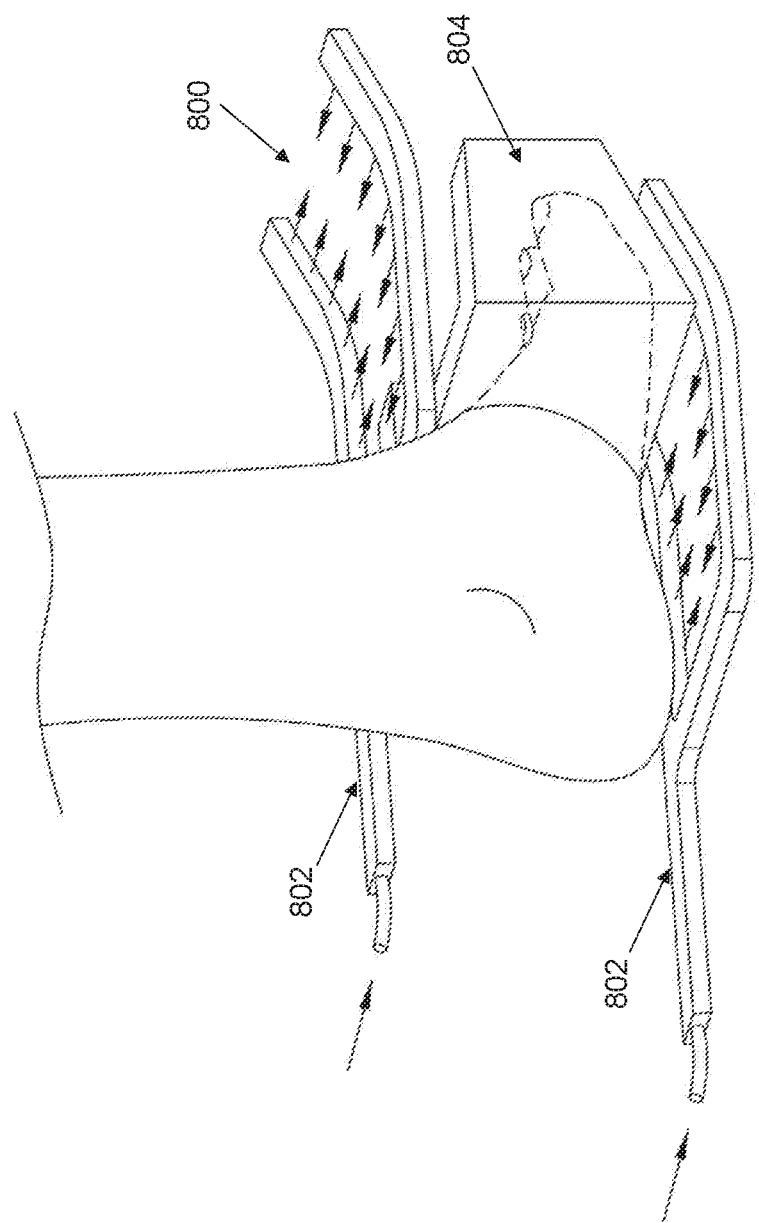
FIG. 8 is a perspective view of another alternative embodiment of the assembly, showing a U-shaped scaffold partition member that is adapted to receive the front of the foot, in accordance with an exemplary embodiment of the present invention.

Another embodiment of the invention is illustrated in FIG. 8. Here, the scaffolding partition member 300 is defined by a U-shaped scaffold partition member 800 that is adapted to receive the front of a foot 804 requiring treatment. The U-shaped scaffold partition member 800 is configured to fit around the toes and front of the foot. In one embodiment, the U-shaped scaffold partition member 800 has an upper face and an lower face that are each adhered to a separate gas flow framing structure. The upper and lower faces directs the gas from the gas flow framing structure 802 directly onto the wound of the foot 804. As can be seen in the illustration gas flow traverses both the top and the bottom of the foot 804. This embodiment typically uses a medical dressing cover gauze that is wrapped around the entire wound dressing.

Figure 9:
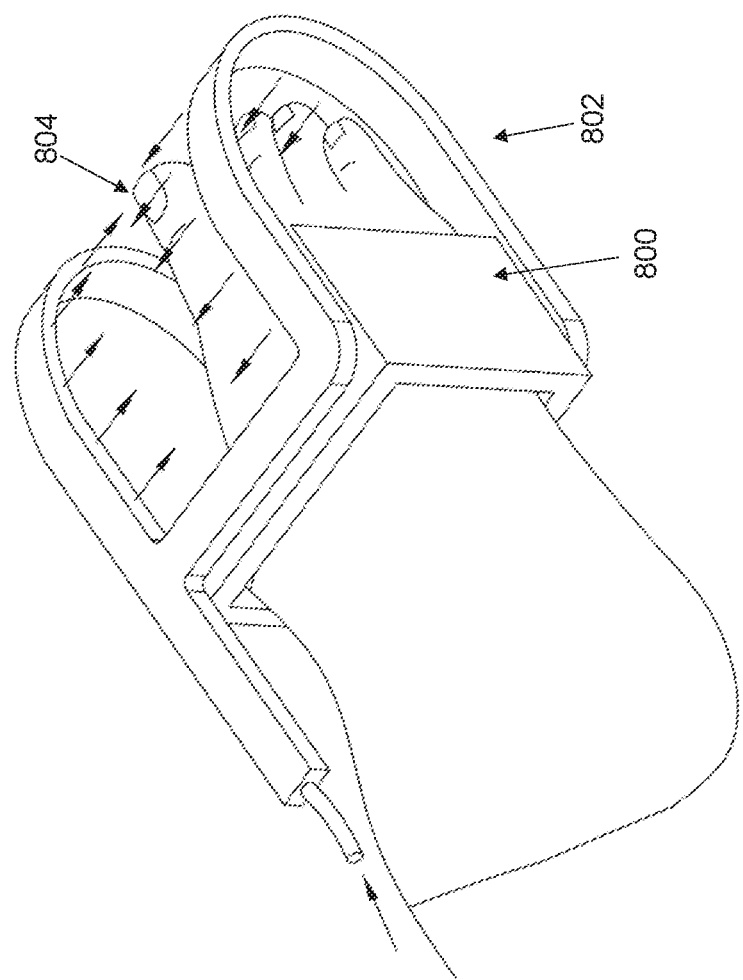
FIG. 9 is a perspective view of another alternative embodiment of the assembly, showing the foot fully fitted inside the U-shaped scaffold partition member, in accordance with an exemplary embodiment of the present invention.

And, as shown in FIG. 9, another embodiment of the invention can be utilized to treat the toes by using the U-shaped scaffold partition member 800 to wrap around the front of the foot 804 directing the flow at the toes. However, it is significant to note that the U-shaped scaffold partition member 800 may be used to treat other parts of the body, such as the hand, ear, or other body parts that can fit into the enclosed area thereof. This embodiment typically uses a medical dressing cover gauze that is wrapped around the entire wound dressing.

Figure 10:
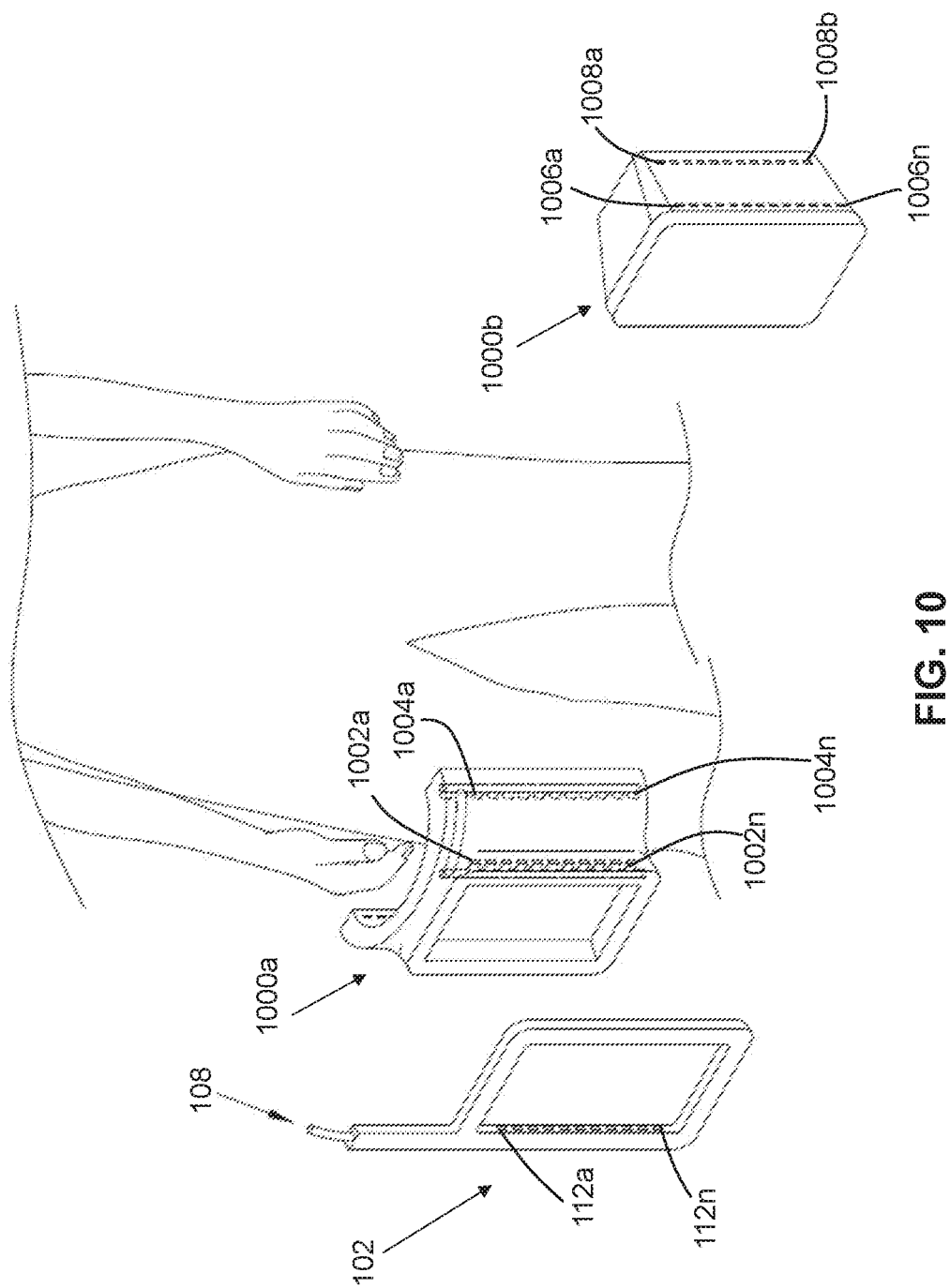
FIG. 10 is a perspective view of another alternative embodiment of the assembly, showing a scaffolding partition member discharging gas flow to a wound near the male reproductive system, and a scaffolding partition member discharging gas flow to a wound near the female reproductive system, in accordance with an exemplary embodiment of the present invention.

Yet another alternative embodiment of the scaffolding partition member is shown in FIG. 10, showing a scaffolding partition member 1000a discharging gas flow to a wound near the male reproductive system, and a scaffolding partition member 1000b discharging gas flow to a wound near the female reproductive system. The male version of the scaffolding partition member 1000a receives gas through inlet ports 1002a-n at an outer surface. The gas discharges through outlet ports 1004a-n at an enclosed inner surface, creating a uniform flow of gas across the wound in the male reproductive system. Conversely, the female version of the scaffolding partition member 1000*b* fits between the thighs of the female and receives the generated gas through inlet ports 1006*a-n* at an outer surface. The gas discharges through outlet ports 1008*a-n* that form along the same outer surface, facing, and carrying gas across the wound in the female reproductive system. This embodiment typically uses a diaper as the medical dressing cover covering the entire wound dressing.

As discussed above, the scaffolding partition member can be configured to fit in multiple body parts, anatomies, and for different genders, age groups, and wound-types. There are a number of embodiments of the scaffolding partition member depending upon the positioning of the gas flow framing structure 102 and the medical dressing cover 200. Many implementations are possible for any body feature including for the following body parts: arms, fingers, toes, hands, and head.

One alternative embodiment utilizes a flexible foam material that adapts standard gas flow framing structure liners to specific skin contours that implements directed or ducted gas flow to wound treatment areas. Single or multiple liners can be used. Implementations with the gas flow framing structure liner integrated into the scaffolding partition member are possible. The scaffolding partition member can be manufactured with existing medical grade equipment. The ability to manufacture specific configurations laser mapping and with 3-D printing allows custom treatment of any wound configuration.

As stated above the primary object of the assembly 400 is to provide a flexible foam material for use with a standard gas flow framing structure liner. With respect to the above description then, it is to be realized that the optimum dimensional relationships for the parts of the invention, to include variations in size, materials, shape, form, and function, are deemed readily apparent and obvious to one skilled in the art, and all equivalent relationships to those illustrated are intended to be encompassed by the present invention In accordance with the present invention, a method 1100 for enhancing the effect of generated gas flow across a wound. The method 1100 includes an initial Step 1102 of identifying a wound area on the skin. The wound 204 may include damage to tissue at a superficial level, or at a deep tissue level. Another Step 1104 may include coupling a gas flow framing structure 102 to a medical dressing covering, the gas flow framing structure defining a gas inlet 108, a gas flow channel 110 within the gas-flow framing structure 102, and a plurality of enclosed gas outlets 112*a-n* operably configured and oriented to direct a generated gas flow 306 therethrough.

Yet another Step 1106 of the method 1100 comprises deforming a resilient scaffolding partition member to fit the contours of the skin near the wound, the scaffolding partition member having an edge defined by a height, the edge creating separation between the gas flow framing structure and the wound area by applying forces to the skin and directing the gas flow. Additionally the scaffolding partition member further can have a plurality of intake ports 700*a-n*, a plurality of outlet ports 702*a-n*, and at least one gas transportation channel 704 internally disposed within the scaffolding partition member 300 and fluidly coupled to the plurality of intake ports 700*a-n* and the plurality of outlet ports 702*a-n*.

The method 1100 may also include a Step 1108 of aligning the plurality of enclosed gas outlets 112*a-n* of the gas-flow framing structure 102 with the plurality of intake ports 700*a-n* of the scaffolding partition member. A Step 1110 comprises engaging the gas flow framing structure with the scaffolding partition member, whereby the edge of the scaffolding partition member creates separation between the medical dressing and the wound, whereby the scaffolding partition member 300 being directly coupled to the gas-flow framing structure 102 in a contouring configuration therewith. The resilience of both the scaffolding partition member and the gas flow framing structure 102 allow for easy coupling, and fitting into the different parts of the body, including skin folds, male reproductive systems, and female reproductive systems.

In one embodiment, a Step 1112 includes introducing the generated gas flow 306 into the gas inlet 108 of the gas-flow framing structure 102, the generated gas flow vents at atmospheric pressure into the wound area. The gas-flow framing structure 102 is configured to introduce a high rate gas flow across a wound 204, so as to enhance treatment of the wound 204. A final Step 1114 comprises directing the gas flow or discharging the gas through the at least one gas transportation channel 704 and the plurality of outlet ports of the scaffolding partition member, whereby the scaffolding partition member increases the treatment volume over the wound.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A dynamic gas-flow wound dressing assembly comprising:
   a medical dressing covering having an upper surface, a lower surface opposing the upper surface;
   a gas flow framing structure coupled to the medical dressing covering, with an outer surface and an inner surface opposing the outer surface of the gas-flow framing structure, and defining a gas inlet, a gas flow channel within the gas-flow framing structure, and a plurality of enclosed gas outlets disposed on the inner surface of the gas-flow framing structure and downstream of the gas inlet, the plurality of enclosed gas outlets each operably configured and oriented to direct a generated gas flow therethrough and to a framing area defined by the inner surface of the gas-flow framing structure and disposed proximal to the lower surface of the medical dressing covering; and
   a scaffolding partition member of a flexible material, with a lower surface without any adhesive disposed thereon, with an outer surface, an inner surface opposing the outer surface of the scaffolding partition member, with an upper surface opposing the lower surface of the scaffolding partition member and having an adhesive material attaching the scaffolding partition member to the gas flow framing structure thereon, and defining an enclosed scaffolding treatment area and scaffolding treatment volume with the inner surface of the scaffolding partition member, the upper surface of the scaffolding partition member selectively removably directly coupled to the gas-flow framing structure in a contouring configuration therewith.

2. The assembly according to claim 1, wherein:
   the gas-flow framing structure is enclosed and the upper surface of the scaffolding partition member is directly coupled to the gas-flow framing structure in a contouring configuration surrounding a perimeter defined thereon.

3. The assembly according to claim 1, wherein:
the scaffolding partition member is substantially of a polymeric foam material having a deformably resilient property.

4. The assembly according to claim 2, wherein the scaffolding partition member further defines:
a plurality of intake ports aligned with the plurality of enclosed gas outlets, a plurality of outlet ports, and at least one gas transportation channel internally disposed within the scaffolding partition member and fluidly coupled to the plurality of intake ports and the plurality of outlet ports.

5. The assembly according to claim 4, wherein:
the plurality of intake ports of the scaffolding partition member are defined along the outer surface of the scaffolding partition member.

6. The assembly according to claim 5, wherein:
the plurality of outlet ports of the scaffolding partition member are defined along the inner surface of the scaffolding partition member.

7. The assembly according to claim 1, wherein the scaffolding partition member comprises:
an edge having a height, the edge creating separation between the gas flow framing structure and a wound area on the skin.

8. The assembly according to claim 1, wherein the scaffolding partition member further defines:
a first adaptor and a second adaptor having substantially the same shape and dimension, the first and second adaptors adapted to sandwich the gas flow framing structure in a contouring configuration surrounding the perimeter defined thereon.

9. The assembly according to claim 1, wherein the scaffolding partition member further comprises:
a wedge having a wide end and a narrow end, the narrow end orienting the gas flow framing structure to apply forces to the skin thereby opening the treatment area.

10. The assembly according to claim 9, wherein:
the wedge directs the generated gas flow from gas flow framing structure the to the wound area on the skin.

11. The assembly according to claim 1, wherein the scaffolding partition member further defines:
a U-shaped scaffold partition member having an upper face and a lower face, the scaffold partition member orienting the gas flow framing structure to direct the gas flow towards the wound area on the skin.

12. The assembly according to claim 1, wherein:
the upper surface of the scaffolding partition member comprises an adhesive attachment to the gas flow framing structure.

13. The assembly according to claim 1, wherein:
the generated gas flowing to the scaffolding treatment area is at the atmospheric pressure.

14. A dynamic gas-flow wound dressing assembly comprising:
a medical dressing covering having an upper surface, a lower surface opposing the upper surface;
a gas flow framing structure coupled to the medical dressing covering, with an outer surface and an inner surface opposing the outer surface of the gas-flow framing structure, and defining a gas inlet, a gas flow channel within the gas-flow framing structure, and a plurality of enclosed gas outlets disposed on the inner surface of the gas-flow framing structure and downstream of the gas inlet, the plurality of enclosed gas outlets each operably configured and oriented to direct a generated gas flow comprising air at about atmospheric pressure therethrough, and to a framing area defined by the inner surface of the gas-flow framing structure and disposed proximal to the lower surface of the medical dressing covering; and
a scaffolding partition member of a flexible material, with a lower surface without any adhesive disposed thereon, with an outer surface, an inner surface opposing the outer surface of the scaffolding partition member, with an upper surface opposing the lower surface of the scaffolding partition member and having an adhesive material disposed thereon, with an edge having a height, the edge creating separation between the gas flow framing structure and a wound area on the skin, and defining an enclosed scaffolding treatment area and scaffolding treatment volume with the inner surface of the scaffolding partition member, the upper surface of the scaffolding partition member selectively removably directly coupled to the gas-flow framing structure in a contouring configuration therewith,
the scaffolding partition member further having a plurality of intake ports aligned with the plurality of enclosed gas outlets, a plurality of outlet ports, and at least one gas transportation channel internally disposed within the scaffolding partition member and fluidly coupled to the plurality of intake ports and the plurality of outlet ports.

15. The assembly according to claim 14, wherein the scaffolding partition member further defines:
a scaffold partition member having an outer face and an inner face, the outer face having a plurality of intake ports aligned with the plurality of enclosed gas outlets, a plurality of outlet ports, and at least one gas transportation channel internally disposed within the scaffolding partition member and fluidly coupled to the plurality of intake ports and the plurality of outlet ports, the scaffolding partition member being configured to distribute the gas inward toward male gentile or outward toward female gentile.

16. The assembly according to claim 14, wherein the scaffolding partition member further defines:
a C-shaped scaffold partition member having an outer face and an inner face, the outer face having a plurality of intake ports aligned with the plurality of enclosed gas outlets, a plurality of outlet ports, and at least one gas transportation channel internally disposed within the C-shaped scaffolding partition member and fluidly coupled to the plurality of intake ports and the plurality of outlet ports.

17. A method for enhancing the effect of generated gas flow across a wound, comprising:
identifying a wound area on the skin;
coupling a gas flow framing structure to a medical dressing covering, the gas flow framing structure defining a gas inlet, a gas flow channel within the gas-flow framing structure, and a plurality of enclosed gas outlets operably configured and oriented to direct a generated gas flow therethrough;
deforming a resilient scaffolding partition member to fit the contours of the skin near the wound, the scaffolding partition member having an edge defined by a height, the edge creating separation between the gas flow framing structure and the wound area by applying forces to the skin and directing the gas flow, the scaffolding partition member further comprising a plurality of intake ports, a plurality of outlet ports, and at least one gas transportation channel internally disposed within the scaffolding partition member and fluidly coupled to the plurality of intake ports and the plurality of outlet ports;
aligning the plurality of enclosed gas outlets of the gas-flow framing structure with the plurality of intake ports of the scaffolding partition member;
engaging the gas flow framing structure with the scaffolding partition member, whereby the edge of the scaffolding partition member creates separation between the medical dressing and the wound, whereby the scaffolding partition member being directly coupled to the gas-flow framing structure in a contouring configuration therewith;
introducing the generated gas flow into the gas inlet of the gas-flow framing structure, the generated gas flow being vented at the atmospheric pressure; and
directing the gas from the gas flow framing structure or discharging the gas through the at least one gas transportation channel and the plurality of outlet ports of the scaffolding partition member, whereby the scaffolding partition member increases the treatment volume over the wound.

* * * * *